United States Patent [19]

Holmgren

[11] 4,318,803

[45] Mar. 9, 1982

[54] FECAL FLOTATION APPARATUS

[76] Inventor: Raymond S. Holmgren, 4608 NE. 102nd, Portland, Oreg. 97220

[21] Appl. No.: 167,926

[22] Filed: Jul. 14, 1980

[51] Int. Cl.$^3$ ............................................. B03B 7/00
[52] U.S. Cl. .................................... 209/17; 210/927; 422/101; 206/229
[58] Field of Search ............... 435/293, 294, 301, 296, 435/810, 30; 220/20.5, 22; 206/229, 569, 45.34; 422/99, 101, 102; 210/927; 209/17, 173

[56] References Cited

U.S. PATENT DOCUMENTS

| | | | |
|---|---|---|---|
| 3,661,265 | 5/1972 | Greenspan | 210/927 |
| 3,819,045 | 6/1974 | Greenwald | 422/99 |
| 3,905,895 | 9/1975 | Addis | 209/173 |
| 3,936,373 | 2/1976 | Studer | 209/173 |
| 4,007,012 | 2/1977 | Greenwald | 206/229 |
| 4,032,437 | 6/1977 | Greenwald | 209/17 |
| 4,057,499 | 11/1977 | Buono | 210/927 |
| 4,225,423 | 9/1980 | Cotey | 209/17 |

Primary Examiner—Benoit Castel
Attorney, Agent, or Firm—Kolisch, Hartwell & Dickinson

[57] ABSTRACT

An apparatus for preparing a liquid suspension of particles, such as an aqueous suspension of parasite eggs, for microscopic examination. The apparatus includes a vial for holding the suspension and a plunger in the form of a tubular cup having a perforated base through which the suspension is displaced, upwardly into the cup, as the plunger is lowered into the vial. The plunger's base functions as a filter selective for particle size. The apparatus is intended to be used by placing at least a predetermined amount of suspension in the vial, and inserting the plunger in the vial until a convex crown forms at the plunger's open upper end. The suspension particles are collected by touching an examination slide to the crown so formed.

1 Claim, 5 Drawing Figures

U.S. Patent  Mar. 9, 1982  4,318,803
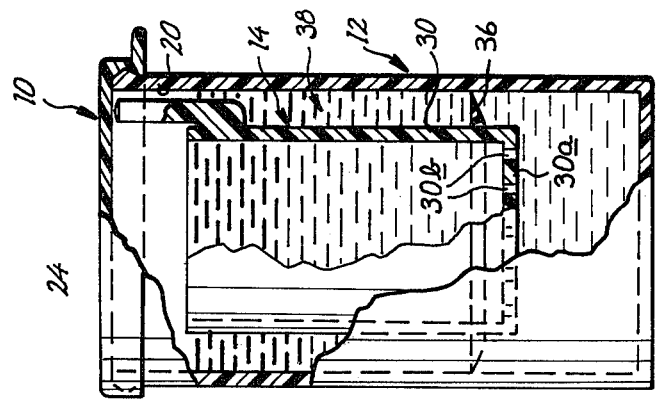
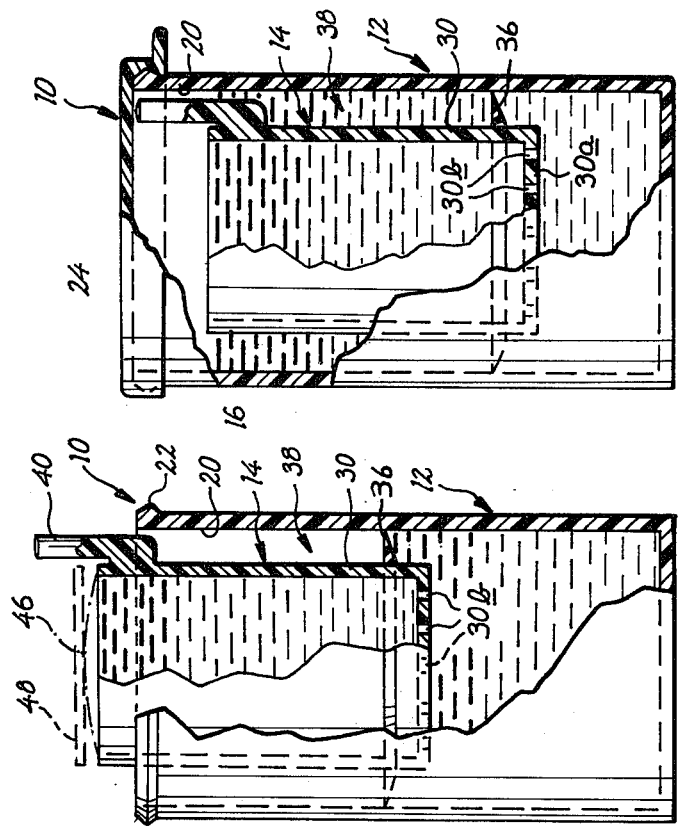
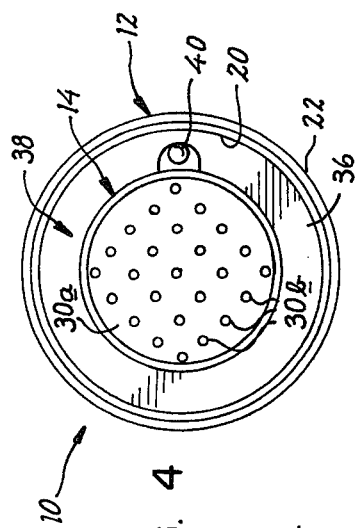
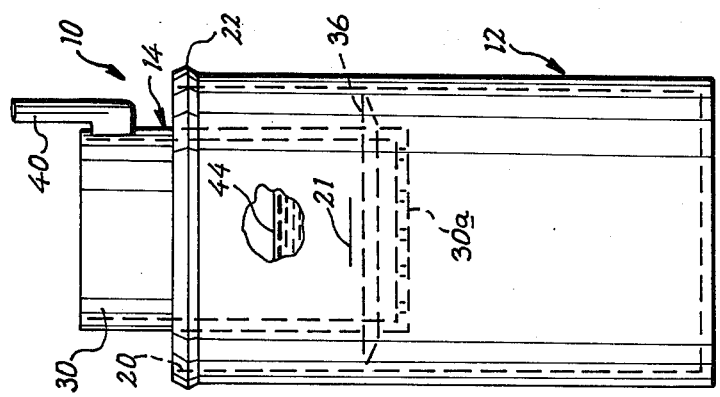
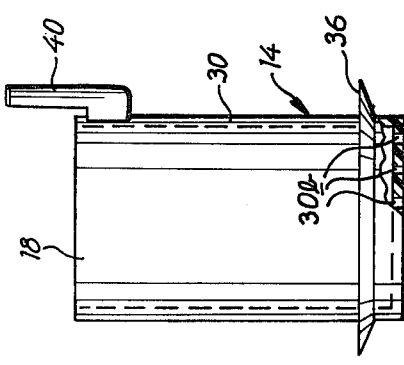

FECAL FLOTATION APPARATUS

BACKGROUND AND SUMMARY OF THE INVENTION

The present invention relates to a diagnostic apparatus, and more particularly, to an apparatus for preparing a liquid suspension of particles, such as an aqueous suspension of parasite eggs, for microscopic examination.

It is routine in medical and veterinary practice, where endoparasites are suspected, to analyze the host's fecal material for the presence of endoparasite eggs. In one common fecal analysis test, the fecal material is placed in a vial, suspended in a quantity of a flotation medium, and filtered to remove larger-than-desired particles. The vial is then completely filled with medium until a convex crown is formed at the vial's upper opening. Particles in the suspension are transferred to an examination slide by touching the slide to the crown.

The just-described fecal analysis procedure is somewhat inefficient in that flotation liquid must be added to the vial twice, once to suspend the fecal sample, and again to raise the level of the suspension to form a crown. Further, if the vial is overfilled, or not carefully handled when filled, the suspension may overflow the vial and contaminate the area where the test is being conducted. Also, after completion of the test, it may be difficult to dispose of the filled vial without additional contamination problems.

One general object of the present invention is to provide an apparatus in fecal analysis which substantially overcomes problems noted above associated with prior art fecal analysis techniques.

Another object of the invention is to provide an apparatus more generally usable to prepare a suspension of particles for assay by examination.

Still another object of the invention is to provide such apparatus which is constructed to minimize the possibility of sample contamination both during and after a test is performed.

Still another object of the invention is to provide apparatus which may be used in combination with commercially available, conventional disposable vials in perfoming suspensionparticle analysis.

The apparatus of the present invention includes a vial for holding a liquid suspension of particles, such as an aqueous suspension of parasite eggs. A tubular cup-like plunger, which is insertable in the vial, receives, through a perforated base, suspension which is displaced upwardly as the plunger is lowered into the vial. Such base acts as a filter for selectively passing suspension particles according to particle size.

The apparatus is intended to be used by placing at least a predetermined amount of suspension in the vial and inserting the plunger into the vial until a convex crown is formed at the plunger's upper open end. The suspension is collected by touching a slide to the crown.

After suspension particles have been transferred to the examination slide, the plunger is pushed fully into the vial, causing liquid in the tube to spill into an annular space between the vial and the plunger. The vial is then capped to seal completely the contents therein, and discarded.

These and other objects and features of the present invention will become more fully apparent when the following detailed description of a preferred embodiment of, and method of practicing, the invention is read in connection with the accompanying drawings, wherein:

FIG. 1 is a side view of a vial and plunger constructed according to the present invention;

FIG. 2 is a view similar to FIG. 1, but showing the plunger inserted in the vial;

FIG. 3 is a partially cutaway view, similar to FIG. 2, illustrating the apparatus in a sample-collection condition;

FIG. 4 is a top view taken generally along line 4—4 in FIG. 2; and

FIG. 5 is a cutaway side view of the apparatus in a sealed condition suitable for disposal.

DETAILED DESCRIPTION OF THE INVENTION

Looking at the figures, there is shown generally at 10 diagnostic apparatus constructed according to the present invention. Very generally, apparatus 10 includes a vial 12 and a plunger 14 which is insertable in the vial (see FIGS. 2, 3 and 5).

Vial 12 is a substantially cylindrical liquid-receiving bottle having an upper opening 20. The vial employed in apparatus 10 may be a standard-size transparent plastic pill vial of a type commercially available, with plunger 14 being designed specifically for use therewith. In such case, only plunger 14 need be supplied to the user thus reducing the cost and packaging size of the supplied goods.

A fill line 21 on the side of vial 12 indicates the desired level of liquid in the vial when conducting the assay procedure to be described below. Line 21 may be affixed to the vial either before or after its being received by the user, depending upon whether the vial forms a part of the supplied goods. The vial additionally includes a flanged lip 22 which is engageable with a deformable tight-fitting plastic cap 24, as seen in FIG. 5, to seal the vial.

Plunger 14 takes the form of a tubular cup 30 which, as can be seen in FIG. 5, is dimensioned to be fully receivable within vial 12. Cup 30 includes a base 30a having perforations 30b which together act as a filter. These perforations are dimensioned to prevent the passage therethrough of particle sizes greater than a predetermined size. In the instant embodiment which is intended for use in fecal analysis, the perforations are dimensioned to pass a variety of different endoparasite eggs, but to prevent passage of larger suspended fecal material. Characteristically, such perforations have a diameter of about 1-mm. While plunger 14 herein is shown as a unitary cup construction, it could, of course, be made in other ways. For example, it could take the form of a tube, or wall portion, with an independent filter web suitably joined adjacent the tube's base.

An annular, resiliently flexible seal 36 encircles cup 30, adjacent the lower end thereof in the figures, and is attached thereto, as by gluing. Seal 36 is dimensioned to form an annular seal between the inner wall of vial 12 and the outer wall of cup 30, when plunger 14 is inserted in the vial, as seen in FIGS. 2-5. The resilience of seal 36 accommodates the plunger to vials having different inner diameters within a small range, and to certain tapered vials. As seen best in FIG. 3, when plunger 14 is inserted in vial 12, seal 36 acts to prevent fluid in the vial from entering the annular space 38 formed between the walls of the vial and the plunger, above seal 36. Consequently, as the plunger is moved downwardly into vial 12, and seal 36 contacts liquid therebelow, liquid in the vial is displaced upwardly into cup 30, through base 30a.

Plunger 14 may include means for guiding the cup axially in the vial. While not shown in the figures, such means may take the form of angularly spaced ribs or protuberances projecting from the cup's outer surface and dimensioned somewhat radially inwardly of the seal's perimeter.

Completing a description of plunger 14, a handle 40 is attached to the side of cup 30, and extends above the cup's upper end as shown. Handle 40 is used in handling the plunger during the operation of apparatus 10, in a manner and for a purpose to be described shortly.

The method of using apparatus 10 to prepare sample particles for examination will now be considered. Initially, a sample, such as a solid fecal sample, is collected and placed in vial 12. The sample, such as the one indicated by dash-dot lines at 42 in FIG. 1, may be pre-weighed, or its volume predetermined, in a conventional manner before being placed in the vial. A suitable suspension medium is added to the vial to the level of line 21. In a typical fecal analytical procedure, the suspension medium includes a salt solution whose density is somewhat greater than the density of the endoparasitic eggs to be assayed. A typical suspension liquid used in assaying for endoparasitic eggs is a sodium nitrate solution having a density of about 1.2 times the density of water. A suspension of sample, such as sample 42 in the just-mentioned medium, is prepared by vigorously mixing the sample in the liquid with a spatula or the like. The amount of suspension prepared in vial 12 which fills the vial to line 21 is also referred to herebelow as a predetermined amount of suspension.

Holding plunger 14 by handle 40, the user inserts the plunger in the vial. This action, as noted above, creates an annular space between the sides of the vial and the plunger, above seal 36. When the plunger is moved to a position within vial 12 bringing the seal 36 in contact with the upper level of liquid therein, continued downward movement of the plunger acts to displace suspension in the vial through base 30a. This is illustrated best in FIG. 2, which shows the level 44 of suspension within cup 30 above line 21. It is noted here that base 30a and perforations 30b act to filter the particles entering the cup. In the present case, performations 30b allow the passage therethrough of endoparasitic eggs or ova, but prevent the passage of larger sample particles.

Continued downward movement of plunger 14 into vial 12 produces further displacement of the suspension in the vial upwardly in cup 30. Ultimately, the suspension in the cup reaches the cup's upper end, and forms thereat a convex crown 46. It will be appreciated that the original volume of suspension in vial 12, to line 21, is sufficient to provide for the complete filling of cup 30 when the cup is inserted to the condition in FIG. 3.

In lowering plunger 14 into vial 12, to produce the convex crown at the top of the plunger, the user may "overshoot" the original crown produced, causing some of the suspension material to spill over the upper end of the plunger and down its sides. With reference particularly to FIG. 3, it is seen that such spillover material would be caught within space 38, completely within vial 12, and would not produce laboratory contamination.

The suspension is allowed to sit for about 20-minutes, once the crown is produced, to allow suspended eggs to float to the top of the liquid in the cup. A microscope slide, here indicated by dashed lines at 48 in FIG. 3, is touched to the crown to transfer particles in the suspension to the slide. The particles may be stained conventionally if desired. A cover slip is then applied to complete the steps necessary for the preparation of the slide for microscopic examination.

Alternatively, a cover slip may be placed and floated on the convex crown, immediately after such is formed. This cover slip is allowed to float on the crown for a period of about 20-minutes, again to allow the suspended particles to float to the upper surface of the liquid and against the cover slip. The particles on the cover slip may be stained, if desired. The cover slip is placed on a slide to complete the steps in slide preparation.

Following the completion of the fecal flotation assay, the apparatus is prepared for disposal by moving plunger 14 fully into vial 12, and by capping the vial with cap 24. As the plunger is moved downwardly into the vial from the position illustrated in FIG. 3, suspension spills over the top of the tube, into space 38. Thus the suspension is entirely contained within vial 12, regardless of the position of the plunger with respect to the vial. As illustrated in FIG. 5, with plunger 14 moved to a position fully within vial 12, spillover fluid from cup 30 has filled a substantial portion of space 38. Note also that with plunger 14 inserted fully in vial 12, handle 40 extends well above the liquid level in the vial. This insures that the disposal procedure can be accomplished without danger of the user contacting the suspension within the vial. The used, capped vial as illustrated in FIG. 5 is now ready for disposal.

From the foregoing, it can be appreciated how the above-stated objects of the present invention are met. First, the method of practicing the invention is quite simple and efficient, requiring adding suspension fluid to a vial only once, and creating a desired convex crown by inserting a plunger in the vial. Secondly, the construction of the apparatus substantially eliminates the possibility of contaminating the laboratory or user with fecal-particle suspension. This means increased safety for laboratory personnel, and increased efficiency in terms of cleanup time. Thirdly, the apparatus once used can be tightly sealed as a unit for disposal, eliminating the need first to dispose of the liquid contained in the apparatus. Finally, the plunger component of the invention may be constructed for use in combination with a standard-sized disposable vial, thus reducing the cost and size of the goods which are supplied to the user for conducting tests according to the present method.

While a preferred embodiment of the present apparatus, and a method for using the same, have been disclosed herein, it is obvious that various changes and modifications can be made without departing from the spirit of the invention.

It is claimed and desired to secure by Letters Patent:

1. Apparatus usable in diagnosing the presence, in a liquid suspension, of particles having a size less than a predetermined size, said apparatus comprising
    a liquid-receiving vial having an upper opening,
    a tubular plunger adapted for insertion in said vial to create a space between the inside of the vial and the outside of the plunger, said plunger having an upper opening and being dimensioned to be pleaceable fully into said vial,
    a filter in said plunger including openings sized for allowing passage therethrough of particles having sizes up to, but not exceeding, said predetermined size, sealing means joined to the outside of said plunger for interposition between the vial and plunger, when the latter is inserted in the former, to form a substantially fluid-tight seal therebetween, said plunger and sealing means being constructed to enable formation of a convex liquid crown at the plunger's upper opening, above the vial's upper opening as the plunger is inserted into the vial, with the vial containing a selected quantity of such suspension, handle means on said plunger, extending above the vial's upper opening, enabling manipulation of said plunger fully into said vial, said plunger, sealing means and handle means being constructed to enable complete insertion into said vial, where the vial contains such a quantity of such suspension, without spillover of liquid from said vial, and a cap which is attachable to said vial's upper opening to seal said vial.

* * * * *